US 8,568,741 B2

(12) United States Patent
Mehdi

(10) Patent No.: US 8,568,741 B2
(45) Date of Patent: Oct. 29, 2013

(54) BOTULINUM TOXIN FOR SMOKING CESSATION

(76) Inventor: Abbas Mehdi, Fresno, CA (US)

( * ) Notice: Subject to any disclaimer, the term of this patent is extended or adjusted under 35 U.S.C. 154(b) by 0 days.

(21) Appl. No.: 13/410,017

(22) Filed: Mar. 1, 2012

(65) Prior Publication Data

US 2013/0230500 A1 Sep. 5, 2013

(51) Int. Cl.
*A61K 38/48* (2006.01)
(52) U.S. Cl.
USPC ...................................... 424/239.1; 424/94.1
(58) Field of Classification Search
USPC ...................................... 424/239.1
See application file for complete search history.

(56) References Cited

FOREIGN PATENT DOCUMENTS

WO WO2011041483 A2 * 4/2011 ............. A61K 38/16

OTHER PUBLICATIONS

Muscles of the mouth. Gray's Anatomy from Professional Health system. downloaded on Jul. 6, 2012 from www.prohealthsys.com/anatomy/grays/myology/muscles_of_the_mouth.php. p. 1-5.*
Carruthers and Carruthers. Botulinum Toxin Products Overview. Skin Therapy Letter. vol. 13, No. 6. p. 1-8 (2008).*
Semchyshyn et al. Botulinum Toxin A Treatment of Perioral Rhytides. Dermatol Surg 2003;29:490-495.*

* cited by examiner

*Primary Examiner* — Taeyoon Kim
(74) *Attorney, Agent, or Firm* — Klarquist Sparkman, LLP

(57) ABSTRACT

The invention provides for the use of any form of botulinum toxin, or any enzymatically active derivative thereof, to cause temporary paralysis of the muscles of the lips of the mouth to promote smoking cessation.

18 Claims, 2 Drawing Sheets

SEQUENCE LISTING

<160> NUMBER OF SEQ ID NOS: 1

<210> SEQ ID NO 1
<211> LENGTH: 1296
<212> TYPE: PRT
<213> ORGANISM: Clostridium botulinum

<400> SEQUENCE: 1

Met Gln Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

-continued

```
Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Pro Glu
     50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
                100                 105                 110

Arg Gly Ile Pro Phe Trp Gly Ser Thr Ile Asp Thr Glu Leu Lys
            115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
        435                 440                 445

Ala Leu Asn Asp Leu Cys Ile Lys Val Asn Asn Trp Asp Leu Phe Phe
    450                 455                 460
```

```
Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
            485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
                515                 520                 525

Glu Leu Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
            595                 600                 605

Gln Leu Val Tyr Asp Phe Thr Asp Glu Thr Ser Glu Val Ser Thr Thr
        610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
                675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
            725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
        755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880
```

```
Leu Arg Tyr Glu Ser Asn His Leu Ile Asp Leu Ser Arg Tyr Ala Ser
            885                 890                 895

Lys Ile Asn Ile Gly Ser Lys Val Asn Phe Asp Pro Ile Asp Lys Asn
        900                 905                 910

Gln Ile Gln Leu Phe Asn Leu Glu Ser Ser Lys Ile Glu Val Ile Leu
        915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
            965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
            995                1000               1005

Asp Tyr Ile Asn Arg Trp Ile Phe Val Thr Ile Thr Asn Asn Arg
            1010               1015               1020

Leu Asn Asn Ser Lys Ile Tyr Ile Asn Gly Arg Leu Ile Asp Gln
        1025               1030               1035

Lys Pro Ile Ser Asn Leu Gly Asn Ile His Ala Ser Asn Asn Ile
        1040               1045               1050

Met Phe Lys Leu Asp Gly Cys Arg Asp Thr His Arg Tyr Ile Trp
        1055               1060               1065

Ile Lys Tyr Phe Asn Leu Phe Asp Lys Glu Leu Asn Glu Lys Glu
        1070               1075               1080

Ile Lys Asp Leu Tyr Asp Asn Gln Ser Asn Ser Gly Ile Leu Lys
        1085               1090               1095

Asp Phe Trp Gly Asp Tyr Leu Gln Tyr Asp Lys Pro Tyr Tyr Met
        1100               1105               1110

Leu Asn Leu Tyr Asp Pro Asn Lys Tyr Val Asp Val Asn Asn Val
        1115               1120               1125

Gly Ile Arg Gly Tyr Met Tyr Leu Lys Gly Pro Arg Gly Ser Val
        1130               1135               1140

Met Thr Thr Asn Ile Tyr Leu Asn Ser Ser Leu Tyr Arg Gly Thr
        1145               1150               1155

Lys Phe Ile Ile Lys Lys Tyr Ala Ser Gly Asn Lys Asp Asn Ile
        1160               1165               1170

Val Arg Asn Asn Asp Arg Val Tyr Ile Asn Val Val Val Lys Asn
        1175               1180               1185

Lys Glu Tyr Arg Leu Ala Thr Asn Ala Ser Gln Ala Gly Val Glu
        1190               1195               1200

Lys Ile Leu Ser Ala Leu Glu Ile Pro Asp Val Gly Asn Leu Ser
        1205               1210               1215

Gln Val Val Val Met Lys Ser Lys Asn Asp Gln Gly Ile Thr Asn
        1220               1225               1230

Lys Cys Lys Met Asn Leu Gln Asp Asn Asn Gly Asn Asp Ile Gly
        1235               1240               1245

Phe Ile Gly Phe His Gln Phe Asn Asn Ile Ala Lys Leu Val Ala
        1250               1255               1260

Ser Asn Trp Tyr Asn Arg Gln Ile Glu Arg Ser Ser Arg Thr Leu
        1265               1270               1275
```

-continued

```
Gly Cys Ser Trp Glu Phe Ile Pro Val Asp Asp Gly Trp Gly Glu
    1280            1285                1290

Arg Pro Leu
    1295
```

BOTULINUM TOXIN FOR SMOKING CESSATION

INCORPORATION BY REFERENCE

The sequence listing contained in the computer-readable 12 KB text file entitled "AMH-001.01_ST.25", created Mar. 19, 2012, is incorporated in its entirety herein by reference.

BACKGROUND OF THE INVENTION

Smoking poses a serious threat to global health. In the United States alone, annual mortality from smoking (including environmental exposure, i.e. "second-hand smoke") surpasses 443,000. Furthermore, smoking significantly increases the risk of various diseases such as coronary artery disease, stroke, lung cancer, and chronic obstructive pulmonary disease. An estimated 46 million people in the United States are smokers, 20.6 percent of the US population.

More than 40 percent of existing smokers attempt to quit smoking annually. Various approved therapies (Chantix™, bupropion, nicotine patch/gum, hypnotherapy, biofeedback) have long been in clinical use to treat nicotine dependence. Existing therapies directed toward smoking cessation tend to focus on counseling, behavioral treatment such as hypnosis, or chemical/pharmaceutical therapies. Overall there are mixed results from current therapeutic options. Each of these agents have only shown moderate efficacy, as evidenced by the present rate of only 10% successful abstinence annually. There seems to be a time period (first 2-4 weeks) where smokers struggle with craving and anxiety. Current literature indicates that both Chantix™ and bupropion have very low (less than 25%) success rates in the first few weeks of treatment intervention.

Given the immense harm of smoking to the human body, the high degree of cost to the health care system, the addictive nature of smoking, and the high level of treatment resistance with respect to conventional therapy, there remains an acute need for effective strategies for smoking cessation.

The anaerobic, gram positive bacterium *Clostridium botulinum* produces a potent polypeptide neurotoxin, botulinum toxin, which causes a neuroparalytic illness in humans and animals referred to as botulism. Eight serotypes, A-G (including $C_1$ and $C_2$), are known. Botulinum toxin type A is the most lethal natural biological agent known to man.

Botulinum toxin comprises a two-chain protein composed of a light chain (molecular weight ca. 50 kDa) covalently bound by a single disulfide bond to a heavy chain (molecular weight ca. 100 kDa). Hence, the molecular weight of each two-chain protein for all known botulinum toxins is about 150 kDa. The light chain bears the domain which exhibits intracellular biological (protease) activity, while the heavy chain comprises the receptor binding (immunogenic) and cell membrane translocational domains.

The various serotypes of botulinum toxin occur in nature as complexes comprising the 150 kDa core two-chain protein associated with certain non-toxin proteins. Thus, the botulinum toxin type A complex can be produced by Clostridial bacteria as 300 kDa, 500 kDa and 900 kDa forms. Botulinum toxin types B and $C_1$ are produced as 500 kDa and 700 kDa complexes. Botulinum toxin type D is produced as both 300 kDa and 500 kDa complexes. Botulinum toxin types E and F are produced only as approximately 500 kDa complexes. The botulinum toxin complexes are believed to contain a non-toxin hemagglutinin protein and a non-toxin non-hemagglutinin protein. These two non-toxin proteins are believed to stabilize botulinum toxin against denaturation and to protect botulinum toxin against digestive acids when it is ingested. Additionally, it is possible that the larger (greater than about 150 kDa molecular weight) botulinum toxin complexes may result in a slower rate of diffusion of the botulinum toxin away from a site of intramuscular injection of a botulinum toxin complex.

Botulinum toxins have been used in clinical settings for the treatment of neuromuscular disorders characterized by hyperactive skeletal muscles. In 1989 a type A botulinum toxin was first approved by the U.S. Food and Drug Administration (FDA) for clinical use in the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia.

Botulinum toxin also has been proposed for or has been used to treat skin wounds (U.S. Pat. No. 6,447,787), various autonomic nerve dysfunctions (U.S. Pat. No. 5,766,605), tension headache, (U.S. Pat. No. 6,458,365), migraine headache (U.S. Pat. No. 5,714,468), sinus headache (U.S. patent application publication 2004/0219172-A1), post-operative pain and visceral pain (U.S. Pat. No. 6,464,986), neuralgia pain (U.S. patent application publication 2004/0028706-A1), hair growth and hair retention (U.S. Pat. No. 6,299,893), fibromyalgia (U.S. Pat. No. 6,623,742), various skin disorders (U.S. patent application publication 2005/0123567-A1), motion sickness (U.S. patent application publication 2005/0147625-A1), psoriasis and dermatitis (U.S. Pat. No. 5,670,484), injured muscles (U.S. Pat. No. 6,423,319), various cancers (U.S. Pat. No. 6,139,845), smooth muscle disorders (U.S. Pat. No. 5,437,291), down-turned mouth corners (U.S. Pat. No. 6,358,917), nerve entrapment syndromes (U.S. patent application publication 2003/0224019-A1), various impulse disorders (U.S. patent application publication 2004/0213811-A1), acne (WO 03/011333), and neurogenic inflammation (U.S. Pat. No. 6,063,768).

Botulinum toxin A is presently commercially available as Botox™ (Allergan, Inc., Irvine, Calif.), Dysport™ (Ipsen, Berkshire, UK), and Xeomin™ (Merz, Frankfurt, Germany). Another botulinum toxin type A drug, PurTox™ (Mentor, Santa Barbara, Calif.), is currently in the FDA regulatory process. Meditoxin™ (Medy-Tox, Seoul, Korea), also known as Neuronox™ or Siax™, is a type A botulinum toxin available internationally and is in clinical trials in the United States. Another type A botulinum toxin is currently marketed in Brazil as Prosigne™ (Lanzhou Institute of Biological Products, China). The success of botulinum toxin A to treat a variety of clinical conditions has led to interest in other botulinum toxin serotypes. Botulinum toxin type B is commercialized as Neurobloc™/Myobloc™ (Solstice Neuroscience, Inc., San Francisco, Calif.).

SUMMARY OF THE INVENTION

An aspect of the invention is a method for smoking cessation. The method includes the step of administering an effective amount of a botulinum toxin, or an enzymatically active derivative thereof, to a muscle of the lips of the mouth to inhibit the lips from forming a seal around a substantially cylindrical object adapted for smoking (5 to 22 millimeters in diameter). In one embodiment, the substantially cylindrical object is a cigarette. In one embodiment, the muscle of the lips to which botulinum toxin is administered is selected from the group consisting of orbicularis oris, mentalis, depressor labii oris, levator labii superioris, zygomaticus minor, and any combination thereof. In one embodiment, the muscle of the lips is the orbicularis oris muscle.

In one embodiment, the botulinum toxin is botulinum toxin A. In one embodiment, the effective amount is the amount required to produce the same maximum paralytic effect as 20 to 80 units of onabotulinumtoxinA. In one embodiment, the botulinum toxin A may be selected from the group consisting of incobotulinumtoxinA, onabotulinumtoxinA, abobotulinumtoxinA, and purified botulin toxin A. In one embodiment, the botulinum toxin is onabotulinumtoxinA in an amount of 20 to 80 units. In one embodiment, the botulinum toxin is incobotulinumtoxinA in amount of 20 to 80 units. In one embodiment, the botulinum toxin is abobotulinumtoxinA in an amount of 40 to 200 units. In one embodiment, the botulinum toxin is purified botulinum toxin A in an amount of 20 to 120 units.

In one embodiment, the botulinum toxin is botulinum toxin B. In one embodiment, the botulinum toxin B is rimabotulinumtoxinB. In one embodiment, the effective amount of rimabotulinumtoxinB is 1000 to 8000 units.

In one embodiment, the botulinum toxin is injected at two or more sites.

In one embodiment, the botulinum toxin is administered to a subject who is not receiving and has not received a botulinum toxin for the treatment of facial spasm or for cosmetic purposes.

DETAILED DESCRIPTION OF THE INVENTION

Figure 1:
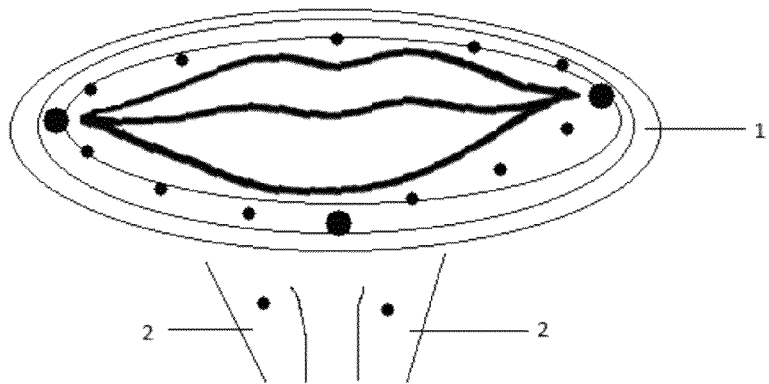
FIG. 1 is a drawing depicting an example of a low-dose administration involving injection of 16 sites with a total dose of approximately 50 units. The darkened circles indicate locations of botulinum toxin administration. Large circles indicate a full dose (4.5-5.0 units), and small circles indicate a half-dose (2.0-2.5 units). Each site receiving $1/19$ of the total dose are two sites within the bilateral mentalis muscle (2), five sites within the orbicularis oris muscle (1) above the upper lip, and six sites within the orbicularis oris muscle below the lower lip. Each of the three other sites, the corners of the mouth and below the lower lip (center), is injected with $2/19$ of the total dose.

This invention provides for the use of any form of botulinum toxin to cause temporary paralysis of the muscles of the lips of the mouth to promote smoking cessation. Complete or partial paralysis of the orbicularis oris muscle, alone or in conjunction with complete or partial paralysis of the mentalis muscle, induces a therapeutic effect by restricting the usual oral action needed for smoking, thereby restricting smoke inhalation through the mouth. Other muscles involved in the physical act of smoking and which also may be injected with botulinum toxin in accordance with the invention include the depressor labii oris, levator labii superioris, and zygomaticus minor.

Rounding or pursing of lips (the process by which the corners of lips are drawn together) is mainly achieved by the action of the orbicularis oris muscle. The orbicularis oris muscle is a circular muscle that encircles the top and bottom lips of the mouth. Injecting into the orbicularis oris muscle at multiple sites a quantity of botulinum toxin sufficient to produce its complete or partial paralysis prevents the rounding or pursing of the lips.

Protrusion or pushing forward (and/or upward) of the lips mainly involves the lower lip and is achieved mainly by the action of the mentalis muscle. The mentalis muscle is a paired central muscle of the lower lip, situated at the tip of the chin. It raises and pushes up the lower lip, causing wrinkling of the chin, as in doubt or displeasure. Injecting into the mentalis muscle at a single site on both sides of the muscle or at multiple sites (also bilaterally) a quantity of botulinum toxin sufficient to produce its complete or partial paralysis prevents protrusion or pushing forward of the lips.

As used herein, "botulinum toxin" is any botulinum toxin preparation, including without limitation the 150 kDa two-chain protein alone; the 150 kDa two-chain protein in combination with at least one complexing or otherwise accompanying protein or other additive; an enzymatically active fragment or derivative of the 150 kDa two-chain protein component alone; or an enzymatically active fragment or derivative of the 150 kDa two-chain protein component in combination with at least one complexing or otherwise accompanying protein or other additive. In one embodiment of the invention, the botulinum toxin includes only the 50 kDa light chain of the 150 kDa two-chain protein. In one embodiment of the invention, the set of complexing proteins includes a non-toxin hemagglutinin protein. In another embodiment of the invention, the set of complexing proteins includes a non-toxin non-hemagglutinin protein. In another embodiment of the invention, the set of complexing proteins includes both a non-toxin hemagglutinin protein and a non-toxin non-hemagglutinin protein. In one embodiment of the invention, the complexing or otherwise accompanying proteins are synthetic proteins.

Accordingly, the term "botulinum toxin" as used herein specifically includes, without limitation, a two-chain core ca. 150 kDa botulinum toxin of any of the various serotypes of botulinum toxin, their various complexes, and commercial preparations thereof, as described herein.

Amino acid sequences for botulinum toxin, as well as nucleic acid sequences encoding same, are known. For example, an amino acid sequence for botulinum toxin A is available as GenBank Accession No. P10845 (SEQ ID NO:1), for which the light chain corresponds to amino acid residues 2-448 and the heavy chain corresponds to amino acid residues 449-1296:

```
MQFVNKQFNY KDPVNGVDIA YIKIPNVGQM QPVKAFKIHN

KIWVIPERDT FTNPEEGDLN PPPEAKQVPV SYYDSTYLST

DNEKDNYLKG VTKLFERIYS TDLGRMLLTS IVRGIPFWGG

STIDTELKVI DTNCINVIQP DGSYRSEELN LVIIGPSADI

IQFECKSFGH EVLNLTRNGY GSTQYIRFSP DFTFGFEESL

EVDTNPLLGA GKFATDPAVT LAHELIHAGH RLYGIAINPN

RVFKVNTNAY YEMSGLEVSF EELRTFGGHD AKFIDSLQEN

EFRLYYYNKF KDIASTLNKA KSIVGTTASL QYMKNVFKEK

YLLSEDTSGK FSVDKLKFDK LYKMLTEIYT EDNFVKFFKV

LNRKTYLNFD KAVFKINIVP KVNYTIYDGF NLRNTNLAAN

FNGQNTEINN MNFTKLKNFT GLFEFYKLLC VRGIITSKTK

SLDKGYNKAL NDLCIKVNNW DLFFSPSEDN FTNDLNKGEE

ITSDTNIEAA EENISLDLIQ QYYLTFNFDN EPENISIENL

SSDIIGQLEL MPNIERFPNG KKYELDKYTM FHYLRAQEFE

HGKSRIALTN SVNEALLNPS RVYTFFSSDY VKKVNKATEA

AMFLGWVEQL VYDFTDETSE VSTTDKIADI TIIIPYIGPA

LNIGNMLYKD DFVGALIFSG AVILLEFIPE IAIPVLGTFA

LVSYIANKVL TVQTIDNALS KRNEKWDEVY KYIVTNWLAK

VNTQIDLIRK KMKEALENQA EATKAIINYQ YNQYTEEEKN

NINFNIDDLS SKLNESINKA MININKFLNQ CSVSYLMNSM

IPYGVKRLED FDASLKDALL KYIYDNRGTL IGQVDRLKDK

VNNTLSTDIP FQLSKYVDNQ RLLSTFTEYI KNIINTSILN

LRYESNHLID LSRYASKINI GSKVNFDPID KNQIQLFNLE

SSKIEVILKN AIVYNSMYEN FSTSFWIRIP KYFNSISLNN

EYTIINCMEN NSGWKVSLNY GEIIWTLQDT QEIKQRVVFK

YSQMINISDY INRWIFVTIT NNRLNNSKIY INGRLIDQKP

ISNLGNIHAS NNIMFKLDGC RDTHRYIWIK YFNLFDKELN

EKEIKDLYDN QSNSGILKDF WGDYLQYDKP YYMLNLYDPN

KYVDVNNVGI RGYMYLKGPR GSVMTTNIYL NSSLYRGTKF

IIKKYASGNK DNIVRNNDRV YINVVVKNKE YRLATNASQA

GVEKILSALE IPDVGNLSQV VVMKSKNDQG ITNKCKMNLQ

DNNGNDIGFI GFHQFNNIAK LVASNWYNRQ IERSSRTLGC

SWEFIPVDDG WGERPL
```

The interchain disulfide bond linking the light and heavy chains is formed between cysteine residues 430 and 454 of SEQ ID NO:1.

In one embodiment, the complexing or otherwise accompanying proteins are selected or engineered to produce a desired molecular weight for the botulinum toxin being administered. In one embodiment, the complexing or otherwise accompanying proteins may be selected or engineered to produce a desired rate of diffusion in relevant tissue. In one embodiment, this desired rate of diffusion is a function of the molecular weight of the botulinum toxin being administered.

An "enzymatically active derivative" as used herein is any derivative or variant of a botulinum toxin having at least 20 percent of the paralytic properties of the relevant corresponding parent botulinum toxin moiety. In one embodiment, an enzymatically active derivative includes 1, 2, 3, 4, 5, or 6 amino acid deletions, additions, substitutions, modifications (e.g., glycosylation), or any combination thereof, in the heavy and/or light chain(s) compared to the relevant corresponding parent botulinum toxin moiety. In one embodiment of the invention, the enzymatically active derivative is the native light chain of botulinum toxin A. In one embodiment of the invention, the enzymatically active derivative is a modified light chain of botulinum toxin A comprising 1, 2, 3, 4, 5, or 6 amino acid deletions, additions, substitutions, modifications (e.g., glycosylation), or any combination thereof, relative to native light chain. In one embodiment, the enzymatically active derivative includes a chimeric (fusion) protein comprising all or any part of either polypeptide chain present in the 150 kDa two-chain protein of botulinum toxin A. In various embodiments of the invention, the enzymatically active derivative includes a protein with at least one of the polypeptide chains of the 150 kDa two-chain protein of botulinum toxin A and said protein has at least one alteration with respect to the primary, secondary, or tertiary structure as compared to the 150 kDa two-chain protein. In one embodiment of the invention, the enzymatically active derivative includes all or any part of at least one of the complexing proteins of botulinum toxin type A. In various embodiments, the enzymatically active derivative has at least 20, 30, 40, 50, 60, 70, 80, 90, 95, or 100 percent of the paralytic properties of a corresponding parent botulinum toxin moiety.

Clinical effects of intramuscular botulinum toxin type A injection usually become clinically apparent within one week of injection. The typical duration of clinical effect of injections of botulinum toxin type A may average about three months, although significantly longer periods of therapeutic activity have been reported.

In an embodiment of the present invention, administration of botulinum toxin produces desired therapeutic effect for a period of 2-4 weeks after onset of therapeutic effect. At the conclusion of the period of desired therapeutic effect, or after a reasonable observation period subsequent, the subject may optionally receive another round of toxin administration.

Electromyographic (EMG)-guided needles may be used for injection to determine needle location of a high degree of accuracy, although this technique is generally not required to practice the instant invention.

The level of therapeutic weakness in the injected muscles can be measured using any of a variety of means, including clinical observation, physical/exercise testing, force transducers, and EMG surface electrodes.

In one embodiment, botulinum toxin injection into certain facial muscles required in the process of smoke inhalation can produce desired therapeutic weakness in these muscles for approximately 2-4 weeks (therapeutic period) after onset of therapeutic effect, without any long-term weakness or adverse effects. Weakness of these muscles prevents the physical process of smoking, including forming a seal around a cigarette, or other substantially cylindrical object, during this period. In one embodiment, this temporary therapeutic weakness does not produce any disfigurement, nor does it limit speech, breathing or swallowing during this therapeutic period. In another embodiment, this temporary therapeutic weakness is accompanied by only minor disfigurement, or by only minor limitation of speech, breathing, or swallowing. In one embodiment, this minor disfigurement or limitation is non-life-threatening. In one embodiment, this minor disfigurement or limitation is non-painful.

In accordance with the invention, botulinum toxin can be used either as a primary therapeutic agent or as an adjunct therapeutic agent for smoking cessation.

In an embodiment of the invention, the administration of botulinum toxin is performed in conjunction with the use of one or more adjunct treatments including without limitation varenicline (Chantix™), bupropion, nicotine patch/gum or other replacement, behavioral therapy including but not limited to hypnotherapy, biofeedback, and counseling. The adjunct treatment may be started before the end of the therapeutic period of the botulinum toxin to reduce any anticipated symptoms of craving and withdrawal resulting from the inability to smoke after botulinum toxin administration. In one embodiment, Chantix™ is started at least five days and no earlier than five weeks (35 days) before the end of the therapeutic period of the botulinum toxin. As an illustrative example, 0.5 mg Chantix™ may be administered once a day for days 1-3, 0.5 mg twice a day for days 4 to 7 (1 mg/day total), and 1 mg twice a day (2 mg/day total) from day 8 until the end of Chantix™ therapy. In another embodiment, bupropion is started at least 10 days before the end of the therapeutic period of the botulinum toxin. A typical dose of bupropion for smoking cessation is 150 mg once daily for three days with increase in dose to 150 mg twice daily if the subject is able to tolerate the starting dose. The adjunct therapies may optionally be administered only upon appearance of symptoms of craving or withdrawal after the therapeutic period of the botulinum toxin.

In another embodiment, botulinum toxin is administered as adjunct therapeutic agent after partially successful or unsuccessful primary treatment with a pharmaceutical agent (including without limitation Chantix™ or bupropion) or other treatment (including without limitation nicotine gum/patch, behavioral therapy, biofeedback, or counseling). In one embodiment, the partially successful or unsuccessful primary therapy preceding botulinum toxin administration is at least 12 weeks in duration. In one embodiment, the partially successful or unsuccessful treatment is Chantix™ or bupropion.

In one embodiment, the subject is evaluated to determine whether low, medium, or high dose botulinum toxin administration is appropriate. In one embodiment, the subject is evaluated before injection to determine whether low, medium, or high dose botulinum toxin administration is appropriate. In one embodiment, evaluation is conducted largely on the basis of lip muscle mass. Individual subjects' degrees of lip muscle mass can vary significantly due to factors such as age, sex, race, and other genetic and behavioral differences, including smoking history. If a subject receives a second administration of botulinum toxin, the provider in selecting an appropriate dose may also consider other factors including previous injection status and present state of muscle weakness/flaccidity.

In addition to dose variation, the specific locations of injection sites may also vary based on subject-specific factors as well as the training and experience of the administering provider. Subject-specific factors may include without limitation skin type/condition, amount and distribution of subcutaneous fat, skin color, race, lip hypertrophy, gender, previous injection status, present state of muscle weakness/flaccidity, and subjective preferences.

In various embodiments of the invention, one botulinum toxin type can be substituted for another. In one embodiment, one botulinum toxin type (A-G) may be administered until a loss of clinical response occurs or neutralizing antibodies develop, followed by the administration of another botulinum toxin type. In one embodiment, botulinum toxin type A is administered until loss of clinical response or development of neutralizing antibodies, followed by administration of botulinum toxin type B.

To determine an appropriate dose for substituting one botulinum toxin type for another, one can perform relevant in vivo and/or in vitro assays directly comparing one type to another. For example, relative potencies can be compared in vivo on the basis of the relative doses of toxin that result in 50% lethality in mice (LD50) over 72-96 hours following single-dose intraperitoneal administration. In vitro assays have been developed, based on continuous cell lines such as neuro-2a, PC12, or SK—N—SH cells, as well as primary neurons derived from chicken, mouse or rat spinal cord cells. Additionally, advanced cell-based assays may optionally provide the ability to detect with high specificity and/or sensitivity the development of neutralizing antibodies to botulinum toxin. See e.g. Pellett et al., A Neuronal Cell-based Botulinum Neurotoxin Assay for Highly Sensitive and Specific Detection of Neutralizing Serum Antibodies, *FEBS Lett.* 581(25):4803-8 (2007).

In an embodiment of the invention, a combination of any two or more of the botulinum serotypes A-G can be administered. In one embodiment, this combination is designed to achieve a particular onset and duration of desired therapeutic result.

In various embodiments, one or more additional compounds can be administered prior to, concurrently with, or subsequent to administration of botulinum toxin for enhanced pharmaceutical properties, including but not limited to increased peak effect, reduced immunogenicity, improved stability, or control of allergic reaction or other side effect from toxin administration. It has been reported that the inclusion of a polysaccharide such as hydroxyethyl starch in a botulinum toxin preparation may result in increased potency, improved stability, reduced toxicity, and reduced immunogenicity. (U.S. Pat. No. 7,780,967). In one embodiment, the polysaccharide or other compound is included in place of human albumin or gelatin. It has also been reported that reduced immunogenicity may be achieved by pre-treating a subject with a tolerogizing agent conjugated to a type A botulinum toxin peptide. (U.S. Pat. No. 7,531,179)

In one embodiment of the invention, the dosage used will be the lowest one which is still therapeutically effective. The subject's sensitivity to, and tolerance of, the toxin can be determined in the initial treatment, for example, by administering a low dosage at one site. Additional administrations of the same or different dosages can be provided as needed. It has also been reported that a subject's immunoresistance to botulinum toxin therapy can be determined by detecting the presence or absence of antibodies immunoreactive to a type A botulinum toxin peptide. (U.S. Pat. No. 7,531,179)

Commercially available botulinum toxin can be reconstituted with sterile non-preserved saline or other suitable diluent prior to injection. Dilutions will vary depending upon the botulinum toxin preparation.

The method of the invention has been successfully performed and has resulted in complete abstinence from smoking for one subject.

The following describes preparations of type A botulinum toxin currently on the market or soon expected to be on the market. Any of these preparations can be used in accordance with the invention. The present invention is not in any way limited to these formulations or their analogues. The present invention includes use of future formulations of botulinum toxin which may not yet even be in development.

Botox™

The generic name for Botox™ is onabotulinumtoxinA. Botox™ for injection is a sterile, vacuum-dried purified botulinum toxin type A produced from fermentation of Hall strain *Clostridium botulinum* type A and intended for intramuscular and intradermal use. It is purified from the culture solution by dialysis and a series of acid precipitations to a complex consisting of the neurotoxin and several accessory proteins. The complex is dissolved in sterile sodium chloride solution containing human albumin and is sterile-filtered (0.2 microns) prior to filling and vacuum-drying. The primary release procedure for Botox™ uses a cell-based potency assay to determine the potency relative to a reference standard. The assay is specific to Allergan's products Botox™ and Botox™ Cosmetic. One unit of Botox™ corresponds to the calculated median intraperitoneal lethal dose (LD50) in mice. According to the manufacturer, due to specific details of this assay such as the vehicle, dilution scheme, and laboratory protocols, units of biological activity of Botox™ cannot be directly converted into units of any other botulinum toxin or any toxin assessed with any other specific assay method. The specific activity of Botox™ is approximately 20 units/nanogram of neurotoxin protein complex. Each vial of Botox™ as presently marketed contains either 50 units of *Clostridium botulinum* type A neurotoxin complex, 0.25 mg of human albumin, and 0.45 mg of sodium chloride; 100 units of *Clostridium botulinum* type A neurotoxin complex, 0.5 mg of human albumin, and 0.9 mg of sodium chloride; or 200 units of *Clostridium botulinum* type A neurotoxin complex, 1 mg of human albumin, and 1.8 mg of sodium chloride in a sterile, vacuum-dried form without a preservative.

Dysport™

The generic name for Dysport™ is abobotulinumtoxinA. Botulinum toxin type A, the active ingredient in Dysport™, is a purified neurotoxin type A complex produced by fermentation of Hall strain *Clostridium botulinum* A. It is purified from culture supernatant by a series of precipitation, dialysis, and chromatography steps. The neurotoxin complex is presently composed of the neurotoxin, hemagglutinin proteins and non-toxin non-hemagglutinin protein. Dysport™ is presently commercially supplied in a single-use, sterile vial for reconstitution intended for intramuscular injection. Each vial commercially available at present contains 500 or 300 units of lyophilized abobotulinumtoxinA, 125 micrograms human serum albumin and 2.5 mg lactose. Dysport™ may contain trace amounts of cow's milk proteins. One unit of Dysport™ corresponds to the calculated median lethal intraperitoneal dose (LD50) in mice. The method for performing the assay is specific to Ipsen's product Dysport™. According to the manufacturer, due to differences in specific details such as vehicle, dilution scheme and laboratory protocols for various mouse LD50 assays, units of biological activity of Dysport™ are not interchangeable nor can be directly converted into units of any other botulinum toxin or any toxin assessed with any other specific assay method. In standard clinical practice, however, the number of units of Dysport™ administered tends to be two to two-and-a-half times the number of units of Botox™ administered for the same clinical indication (approximately 2-2.5 to 1 ratio).

Compared to Botox™, Dysport™ has a quicker onset of action (within 1-2 days versus 3-4 days). Clinical research has shown Botox™ to have a longer duration of action than Dysport™ for tested indications: (blepharospasm, 62.2 days vs. 47.4 days (p=0.001); cervical dystonia, 64.3 days vs. 44.6 days (p=0.014); hemifacial spasm, 65.1 days vs. 41.8 days (p<0.014), respectively). Dysport™ may have a higher index of diffusion as compared to Botox™

Xeomin™

The generic name for Xeomin™ is incobotulinumtoxinA. The active ingredient of Xeomin™ is botulinum toxin type A produced from fermentation of Hall strain Clostridium botulinum serotype A. The botulinum toxin complex is purified from culture supernatant and then the active ingredient is separated from the proteins (hemagglutinins and non-hemagglutinins) through a series of steps yielding the active neurotoxin with molecular weight of 150 kDa, without accessory proteins. In one embodiment, Xeomin™ is a sterile lyophilized powder intended for intramuscular injection after reconstitution with preservative-free 0.9% saline. One vial of Xeomin™ as presently marketed contains 50 or 100 units of incobotulinumtoxinA, 1 mg of human albumin, and 4.7 mg sucrose. One unit corresponds to the mouse median lethal dose (LD50) when the reconstituted product is injected intraperitoneally into mice under defined conditions. According to the manufacturer, the method for conducting the assay is specific to Xeomin™, and units of biological activity of Xeomin™ cannot be directly converted into units of any other botulinum toxin assessed with other specific assays. In standard clinical practice, however, the number of units of Xeomin™ administered tends to be substantially similar to the number of units of Botox™ administered for the same clinical indication (approximately 1 to 1 ratio).

PurTox™

The generic name for PurTox™, as used herein, is purified botulinum toxin A. PurTox™ is not presently commercially available but is proceeding through the FDA regulatory process. The active ingredient of PurTox™ is botulinum toxin type A produced from fermentation of Hall strain *Clostridium botulinum* serotype A. The botulinum toxin is purified through a series of steps yielding the active neurotoxin with molecular weight of 150 kDa, without accessory proteins. While not presently used in clinical practice, it is believed that the number of units of PurTox™ prescribed and administered will be somewhat higher than the number of units of Botox™ administered for the same clinical indication (approximately 1-1.5 to 1 ratio).

The following describes a preparation of type B botulinum toxin currently on the market. Such preparation can be used in accordance with the invention.

Myobloc™

The generic name for Myobloc™ is rimabotulinumtoxinB. Botulinum toxin type B of Myobloc™ is produced by fermentation of the bacterium *Clostridium botulinum* type B (Bean strain) and exists in noncovalent association with hemagglutinin and nonhemagglutinin proteins as a neurotoxin complex. The neurotoxin complex is recovered from the fermentation process and purified through a series of precipitation and chromatography steps. Myobloc™ is provided as a clear and colorless to light-yellow sterile injectable solution in 3.5-mL glass vials. Each single-use vial of formulated Myobloc™ contains 5,000 units of botulinum toxin type B per milliliter in 0.05% human serum albumin, 0.01 M sodium succinate, and 0.1 M sodium chloride at approximately pH 5.6. One unit of Myobloc™ corresponds to the calculated median lethal intraperitoneal dose (LD50) in mice. The method for performing the assay is specific to Solstice Neurosciences' manufacture of Myobloc™. According to the manufacturer, due to differences in specific details such as the vehicle, dilution scheme and laboratory protocols for various mouse LD50 assays, units of biological activity of Myobloc™ cannot be compared to or converted into units of any other botulinum toxin or any toxin assessed with any other specific assay method. The specific activity of Myobloc™ ranges between 70 to 130 units/ng.

DEFINITIONS

A "seal" refers in general to anything that tightly or completely closes or secures a thing. As used herein, a "seal" formed by the lips refers to a complete or substantially complete enclosure by the lips of the mouth around a substantially cylindrical object, such as a cigarette, so as to permit active inhalation from the cigarette or other smoking apparatus when the individual attempts to smoke. In one embodiment a seal formed by the lips of the mouth around a substantially cylindrical object is a complete enclosure by the lips of the mouth around the substantially cylindrical object. It may be possible for an individual to smoke with a less than perfect seal. In one embodiment a seal formed by the lips of the mouth around a substantially cylindrical object is a substantially complete enclosure by the lips of the mouth around the substantially cylindrical object. In one embodiment of the invention, administration of botulinum toxin prevents formation of a complete enclosure by the lips of the mouth around the substantially cylindrical object. In one embodiment of the invention, administration of botulinum toxin prevents formation of a substantially complete enclosure by the lips of the mouth around the substantially cylindrical object. In various embodiments of the invention, administration of botulinum toxin reduces by 90%, 80%, 70%, 60%, 50%, 40%, or 30% the amount of suction that is capable of being produced during active inhalation as the subject attempts to smoke. In various embodiments of the invention, administration of botulinum toxin reduces by 90%, 80%, 70%, 60%, 50%, 40%, or 30% the amount of nicotine inhaled, as can be measured in the bloodstream. In one embodiment of the invention, administration of botulinum toxin increases by at least 30% the amount of air flow around the substantially cylindrical object while placed in the subject's mouth as the subject attempts to smoke.

As used herein, "inhibit" means interfere with, prohibit or prevent Inhibition can be complete or partial. In one embodiment of the invention, the inhibition is complete such that there is no active inhalation possible.

"Paralytic effect" as used herein refers to the degree and duration of flaccid paralysis of a treated muscle. "Maximum paralytic effect" as used herein is the maximum degree of paralysis of the target muscle or muscles achieved by the toxin preparation at any time point after administration of the toxin. The degree of paralysis can range, in general, from 0 to 100 percent flaccid paralysis. In one embodiment, maximum paralytic effect is 100 percent paralysis at any time point after administration of the toxin. Full onset may occur earlier for one toxin preparation as compared to another preparation; therefore, maximum paralytic effect is not an attribute measured at any fixed time point after administration.

"Smoking cessation" as used herein refers to discontinuation of smoking behavior. The present invention focuses on cessation of tobacco smoking; however, the methods described also apply to cessation of smoking other substances that can be difficult to stop using due to the development of strong physical substance dependence or psychological dependence. The present invention is directed towards smoking cessation with respect to smoking from any of a number of products or apparatuses, including but not limited to cigarettes (including electronic cigarettes), cigars, pipes, and hookahs (shishas).

"Administering" of botulinum toxin involves directly injecting a target muscle. In one embodiment of the invention, this injection is directly into the belly of the muscle. In one embodiment, the injecting is percutaneous. In this embodiment the injection passes through the skin overlying the muscle and into the muscle. In another embodiment, the injecting is permucosal. In this embodiment the injection passes through the oral mucosa and into the muscle.

In one aspect of the present invention, a method for smoking cessation comprises administering an effective amount of a botulinum toxin, or an enzymatically active derivative thereof, to a muscle of the lips of the mouth of a subject in need thereof to inhibit the lips from forming a seal around a substantially cylindrical object 5 to 22 millimeters in diameter.

In one embodiment of the invention, the substantially cylindrical object is a cigarette. In one embodiment, the substantially cylindrical object is a cigar. In one embodiment, the substantially cylindrical object is a pipe. In one embodiment, the substantially cylindrical object is the mouthpiece of a hookah or shisha.

In one embodiment of the present invention, the muscle of the lips is selected from the group consisting of orbicularis oris, mentalis, depressor labii oris, levator labii superioris, zygomaticus minor, and any combination thereof.

In one embodiment of the present invention, the muscle of the lips is the orbicularis oris.

In one embodiment of the present invention, the botulinum toxin is botulinum toxin A.

In one embodiment of the present invention, the effective amount is the amount required to produce the same maximum paralytic effect as 20 to 80 units of onabotulinumtoxinA.

In one embodiment of the present invention, the botulinum toxin is selected from the group consisting of onabotulinumtoxinA (Botox™), incobotulinumtoxinA (Xeomin™) abobotulinumtoxinA (Dysport™), and purified botulinum toxin A (PurTox™).

In one embodiment of the present invention, the botulinum toxin is onabotulinumtoxinA and the effective amount is 20 to 80 units. In one embodiment of the present invention, the botulinum toxin is onabotulinumtoxinA and the effective amount is 40 to 60 units. For most subjects, 40 to 60 units of onabotulinumtoxinA is sufficient to produce the desired paralytic effect.

In one embodiment of the present invention, the botulinum toxin is incobotulinumtoxinA and the effective amount is 20 to 80 units. In one embodiment of the present invention, the botulinum toxin is incobotulinumtoxinA and the effective amount is 40 to 60 units. For most subjects, 40 to 60 units of incobotulinumtoxinA is sufficient to produce the desired paralytic effect.

In one embodiment of the present invention, the botulinum toxin is abobotulinumtoxinA and the effective amount is 40 to 200 units. In one embodiment of the present invention, the botulinum toxin is abobotulinumtoxinA and the effective amount is 80 to 140 units. For most subjects, 80 to 140 units of abobotulinumtoxinA is sufficient to produce the desired paralytic effect.

In one embodiment of the present invention, the botulinum toxin is purified botulinum toxin A and the effective amount is 20 to 120 units.

In one embodiment of the present invention, the botulinum toxin is botulinum toxin B.

In one embodiment of the present invention, the botulinum toxin is rimabotulinumtoxinB (Myobloc™). In one embodiment of the present invention, the botulinum toxin is rimabotulinumtoxinB and the effective amount is 1000 to 8000 units. In one embodiment, the botulinum toxin is rimabotulinumtoxinB and the effective amount is 2000 to 6000 units.

In one embodiment of the present invention, the administering comprises injecting the botulinum toxin at two or more sites, including but not limited to two sites, three sites, four sites, five sites, six sites, seven sites, eight sites, nine sites, ten sites, eleven sites, twelve sites, thirteen sites, fourteen sites, fifteen sites, sixteen sites, seventeen sites, eighteen sites, and nineteen sites, twenty sites, twenty-one sites, twenty-two sites, twenty-three sites, twenty-four sites, and twenty-five sites.

In one embodiment of the present invention, the subject is not receiving and has not received a botulinum toxin for the treatment of facial spasm or for cosmetic purposes.

Any aspect or embodiment of the invention discussed herein may be interpreted to read upon or be combined with any other aspect or embodiment of the invention.

EXAMPLES

The following are examples of botulinum toxin injection distributions. The injections are not required to be in particular positions within the muscles. The particular locations of injection within the muscle may vary significantly without having appreciable effect on the degree of paralysis obtained. An area of a muscle may be skipped entirely by the administering provider if, for example, it has been previously and/or recently injected.

In one embodiment, a muscle may be injected in multiple locations in one administration, and then only injected in one location on a subsequent injection. In another embodiment, a muscle may be injected in a single location in one administration, and then injected in multiple locations in a subsequent injection. Similarly, in one embodiment, an injection site may receive a lower dose in a subsequent administration as compared to an earlier administration. Or alternatively, in another embodiment, an injection site may receive a higher dose in a subsequent administration as compared to an earlier administration.

Example 1

An example of a lower-dose administration is shown in FIG. 1 and involves injection of 16 sites with a total dose of approximately 50 units of Xeomin™ or Botox™ (or approximately 100 units of Dysport™). Each receiving $1/19$ of the total dose are two sites within the bilateral mentalis muscle, five sites within the orbicularis oris muscle (superior), and six sites within the orbicularis oris (inferior). Each of the three other injection sites, the two corners of the mouth and below the bottom lip (center), is injected with $2/19$ of the total dose.

Example 2

Figure 2:
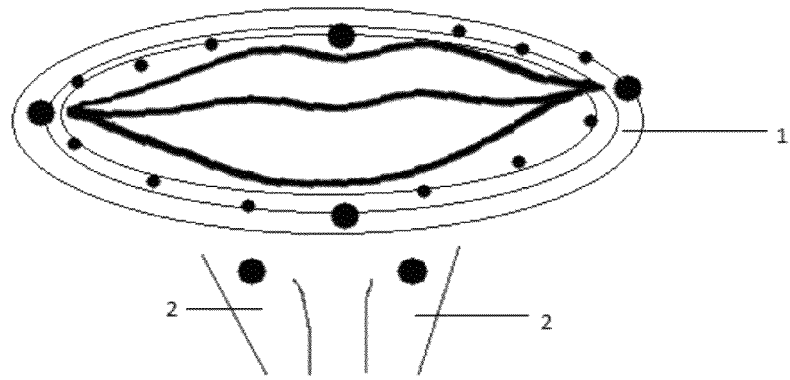
FIG. 2 is a drawing depicting an example of a medium-dose administration involving injection of 18 sites with a total dose of approximately 60 units. The darkened circles indicate locations of botulinum toxin administration. Large circles indicate a full dose (4.5-5.0 units), and small circles indicate a half-dose (2.0-2.5 units). Each receiving $1/24$ of the total dose are six sites within the orbicularis oris muscle (1) above the upper lip and 6 sites within the orbicularis oris muscle (1) below the lower lip. Each receiving $1/12$ of the total dose are six other sites: above the top lip (center), below the bottom lip (center), each corner of the mouth, and two sites in the bilateral mentalis muscle (2).

An example of a medium-dose administration is shown in FIG. 2 and involves injection of 18 sites with a total dose of approximately 60 units of Xeomin™ or Botox™ (or approximately 120 units of Dysport™). Each receiving $1/24$ of the total dose are six sites within the orbicularis oris muscle (superior) and 6 sites within the orbicularis oris muscle (inferior). Each receiving $1/12$ of the total dose are six other sites: above top lip (center), below bottom lip (center), each corner of the mouth, and two sites in the bilateral mentalis muscle.

Example 3

Figure 3:
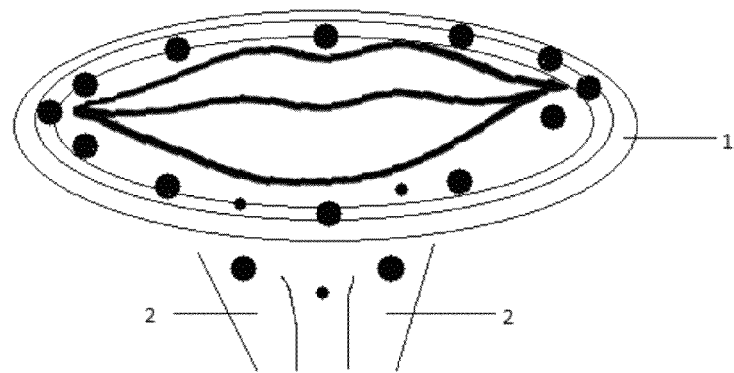
FIG. 3 is a drawing depicting an example of a medium-to-high-dose administration involving injection of 17 sites with a total dose of approximately 70 units. The darkened circles indicate locations of botulinum toxin administration. Large circles indicate a full dose (4.5-5.0 units), and small circles indicate a half-dose (2.0-2.5 units). Each receiving $1/31$ of the total dose are three sites below the lower lip between the mentalis musculature (2). The other 14 sites are each injected with $2/31$ of the total dose.

An example of a medium-to-high-dose administration is shown in FIG. 3 and involves injection of 17 sites with a total dose of approximately 70 units of Xeomin™ or Botox™ (or approximately 140 units of Dysport™). Each receiving $1/31$ of the total dose are three sites below the lower lip between the mentalis musculature. The other 14 sites are each injected with $2/31$ of the total dose.

Example 4

Figure 4:
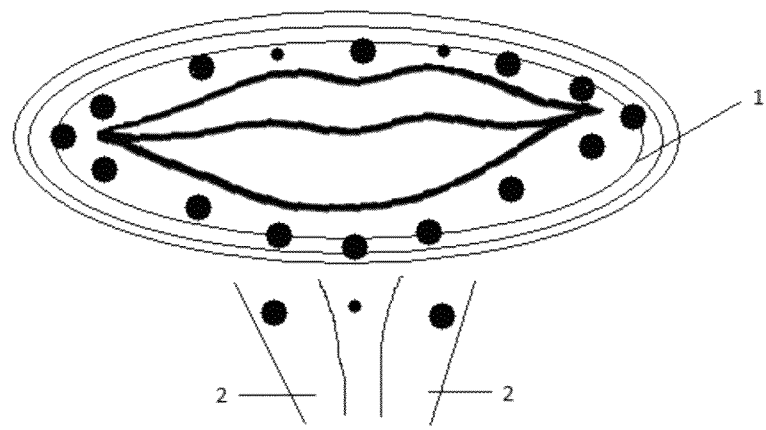
FIG. 4 is a drawing depicting an example of a high-dose administration involves injection of 19 sites with a total dose of approximately 80 units. The darkened circles indicate locations of botulinum toxin administration. Large circles indicate a full dose (4.5-5.0 units), and small circles indicate a half-dose (2.0-2.5 units). Each receiving $1/35$ of the total dose are two sites above the upper lip within the orbicularis oris muscle and one site below the lower lip between the mentalis musculature. The other 16 sites are each injected with $2/35$ of the total dose.

An example of a high-dose administration is shown in FIG. 4 and involves injection of 19 sites with a total dose of approximately 80 units of Xeomin™ or Botox™ (or approximately 150-160 units of Dysport™). Each receiving $1/35$ of the total dose are two sites within the orbicularis oris (superior) and one site below the lower lip between the mentalis musculature. The other 16 sites are each injected with $2/35$ of the total dose.

INCORPORATION BY REFERENCE

All of the U.S. patents and U.S. published patent applications cited herein are hereby incorporated by reference.

Equivalents

Although the present invention has been described in detail with regard to certain preferred methods, other embodiments, versions, and modifications within the scope of the present invention are possible. Those skilled in the art will recognize, or be able to ascertain using no more than routine experimentation, many equivalents to the specific embodiments of the invention described herein. Such equivalents are intended to be encompassed by the following claims.

I claim:

1. A method for promoting smoking cessation, comprising administering an effective amount of a botulinum toxin, or an enzymatically active fragment thereof, to a muscle of the lips of the mouth of a subject in need thereof to inhibit the lips from forming a seal around a substantially cylindrical object 5 to 22 millimeters in diameter, thereby promoting smoking cessation, wherein the subject is not receiving and has not received a botulinum toxin at the muscle for the treatment of facial spasm or for cosmetic purposes.

2. The method of claim 1, wherein the substantially cylindrical object is a cigarette.

3. The method of claim 1, wherein the muscle of the lips is selected from the group consisting of orbicularis oris, mentalis, depressor labii oris, levator labii superioris, zygomaticus minor, and any combination thereof.

4. The method of claim 3, wherein the muscle of the lips is the orbicularis oris.

5. The method of claim 1, wherein the botulinum toxin is botulinum toxin A.

6. The method of claim 1, wherein the botulinum toxin is selected from the group consisting of incobotulinumtoxinA, onabotulinumtoxinA, abobotulinumtoxinA, and a botulinum toxin consisting essentially of a botulinum toxin A having a molecular weight of 150 kDa.

7. The method of claim 1, wherein the effective amount is the amount required to produce the same maximum paralytic effect as 20 to 80 units of onabotulinumtoxinA.

8. The method of claim 1, wherein the botulinum toxin is onabotulinumtoxinA and the effective amount is 20 to 80 units.

9. The method of claim 1, wherein the botulinum toxin is incobotulinumtoxinA and the effective amount is 20 to 80 units.

10. The method of claim 1, wherein the botulinum toxin is abobotulinumtoxinA and the effective amount is 40 to 200 units.

11. The method of claim 1, wherein the botulinum toxin consists essentially of a botulinum toxin A having a molecular weight of 150 kDa and the effective amount is 20 to 120 units.

12. The method of claim 1, wherein the botulinum toxin is botulinum toxin B.

13. The method of claim 1, wherein the botulinum toxin is rimabotulinumtoxinB.

14. The method of claim 1, wherein the botulinum toxin is rimabotulinumtoxinB and the effective amount is 1000 to 8000 units.

15. The method of claim 1, wherein the administering comprises injecting the botulinum toxin at two or more sites.

16. The method of claim 1, wherein the subject is not receiving and has not received a botulinum toxin for the treatment of facial spasm or for cosmetic purposes.

17. The method of claim 1, wherein the effective amount of botulinum toxin, or enzymatically active fragment thereof, is administered to the orbicularis oris and mentalis muscles.

18. The method of claim 15, wherein at least one of the sites is at a corner of the mouth.

* * * * *